United States Patent [19]

Macchio et al.

[11] Patent Number: 5,023,075
[45] Date of Patent: Jun. 11, 1991

[54] MICROFINE COSMETIC POWDER COMPRISING POLYMERS, SILICONE, AND LECITHIN

[75] Inventors: Ralph A. Macchio, Monsey, N.Y.; Julio G. Russ, Germantown, Tenn.; Brent Slobody, New City; Mariene Tietjen, New York, both of N.Y.

[73] Assignee: Revlon, Inc., New York, N.Y.

[21] Appl. No.: 418,678

[22] Filed: Oct. 10, 1989

[51] Int. Cl.$^5$ ............... A61K 7/020; A61K 7/021; A61K 7/035
[52] U.S. Cl. .......................... 424/63; 424/69; 424/78; 424/81; 424/83; 424/401; 424/489; 424/497
[58] Field of Search .............. 424/63, 69, 83, 81, 424/78, 401, 489, 497

[56] References Cited

U.S. PATENT DOCUMENTS

| | | | |
|---|---|---|---|
| 4,246,257 | 1/1981 | Elliott et al. | 424/81 X |
| 4,532,132 | 7/1985 | Keil | 514/772 |
| 4,578,266 | 3/1986 | Tietjen et al. | 424/63 X |
| 4,622,074 | 11/1986 | Miyoshi et al. | 106/419 |

FOREIGN PATENT DOCUMENTS 158295 7/1981 Japan .
95395 11/1986 Japan .

Primary Examiner—Thurman K. Page
Assistant Examiner—Susan S. Rucker

[57] ABSTRACT

A cosmetic containing a powder component and a silicone oil component, said powder component having microfine, low surface energy particles, at least 50% of which have an average particle size of 10 microns, at least 70% being coated with lecithin, and said powder component further containing polymethyl methacrylate, nylon and polyethylene.

13 Claims, No Drawings

MICROFINE COSMETIC POWDER COMPRISING POLYMERS, SILICONE, AND LECITHIN

TECHNICAL FIELD

This invention relates to cosmetic powders in loose or pressed form such as eye shadow, blush, and concealers. More particularly, the invention relates to microfine cosmetic powders containing nylon, polymethyl methacrylate, polyethylene, silicone, and lecithin.

PRIOR ART

U.S. Pat. No. 4,622,074 discloses lecithin coating of pigments but does not show lecithin coating of a plastic polymer, such as nylon.

U.S. Pat. No. 4,246,257 shows spherical particles of a polymer (polymethyl methacrylate, polyethylene or polystyrene) at a particle size of 5-15 microns and a level of 3-10% being used in a unpigmented oil-in-water cosmetic emulsion The patent does not show these polymers being used in a pigmented cosmetic powder.

U.S. Pat. No. 4,578,266 discloses a pigmented cosmetic powder using high levels of a silicone oil, such as dimethyl polysiloxane (CTFA name is dimethicone) as a coating for the pigment material. The patent does not show a low level (below 10%) of dimethyl polysiloxane to achieve the results of this invention.

The prior art has sought to produce light silky, velvety smooth cosmetic powders in loose or pressed form that could be used for a blush, concealer or face powder. Lecithin coating and silicone coating the pigments used in these formulations has improved the smoothness of these powders but even better silky properties are desired. An ideal cosmetic has the following properties: translucent when applied, unpowdery, microfine soft silky-feel, non-pore clogging (allows the skin to breathe) non-drying, non-streaking, true in color, and long wearing.

SUMMARY OF THE INVENTION

It is accordingly an object of this invention to produce a microfine cosmetic face powder containing a high level of pigment which when applied to the skin is translucent, non-pore clogging and ultra-smooth in application.

Another object is to produce a cosmetic having a microfine, silk-like texture by the use of low-surface energy particles, at least 50% having an average particle size of 10 microns, which have improved wetting characteristics, easy dispersability, pronounced softness, excellent spreading over the skin, and are non-drying.

Still another object is to use emollient oils which coat the skin with a light film that provides protection from the harmful effects of the environment while at the same time allowing the skin to breathe.

These and other objects have been achieved by the present invention which comprises a cosmetic containing a powder component and a silicone oil component, said powder component having microfine, low surface energy particles, at least 50% of which have an average particle size of 10 microns, at least 70% being coated with lecithin, and said powder component further containing polymethyl methacrylate, nylon and polyethylene as critical ingredients. These cosmetics are typically face powders, concealers, eye shadows, blush and the like.

DETAILED DESCRIPTION OF THE INVENTION

The cosmetic powder of this invention comprises 10-90% by weight of a powder component and 1-10% by weight of a silicone oil component wherein the powder component has all particles below 30 microns, at least 50% of said particles at an average particle size of 10 microns, and at least 70% of the particles coated with lecithin, said powder component containing 1-6% by weight polyethylene, 1-10% by weight polymethyl methacrylate, 5-25% by weight nylon, 25-75% by weight fillers, and wherein the oil component is a blend of dimethyl polysiloxane (dimethicone) oils having a viscosity of 10-500 centipoises.

As indicated all the particles in the powder component are below 30 microns, preferably below 20 microns. Most preferably, the particles have an average particle size of 10 microns. The polyethylene, nylon, and fillers all have a particle size of below 20 microns. The polymethyl methacrylate has a still smaller critical particle size of below 10 microns. The term "fillers" as used herein includes talc, mica, silica, titanium dioxide, iron oxide, kaolin, and the like.

The ultra smooth feel and softness of this unique face powder is achieved by combining all the above features, i.e. critical particle size of the powder component, the lecithin coating of the powder, the essential powder ingredients of polyethylene, polymethyl methacrylate, nylon, and fillers and the silicone oil component, i.e. a blend of dimethyl polysiloxane oils conforming to the general formula:

$$(CH_3)_3 SiO [Si (CH_3)_2O]_{d-Si(CH_3)_3}$$

in which d is the degree of polymerization, typically between 1 and 1000 effective to give a viscosity of 10 to 500 centipoises. Both a high molecular weight oil of 4000 to 11000 centipoises and a low molecular weight oil of 1 to 10 centipoises are used to achieve the final viscosity. The blend of oils enables all ingredients to be coated thus producing maximum emolliency.

Cosmetic powders in accordance with this invention especially contain 5-25% by weight of spherical nylon particles having an average size of 10 microns. The sphere-like shape of the microscopic nylon particles lowers the surface energy of the powder and provides for excellent spreading over the skin as well as pronounced softness. Nylon has a preferred range of 10-20% by weight and is preferably coated with lecithin to lower the surface energy of the nylon. The lecithin-coated nylon and lecithin-coated fillers account for at least 70% by weight of the particles.

The polymethyl methacrylate polymer has a range of 1-10% by weight but 3-8% is preferred. The particle size of this polymer is below 10 microns, preferably 2-5 microns. This low surface energy polymer imparts an ultra-smooth, dry feel to the final cosmetic product. The final powder glides onto the skin with an effortless application.

The polyethylene is another low surface energy polymer used as a binder at a level of 1-6% by weight with 3-5% being preferred. The particle size of the polyethylene is below 20 microns.

The fillers comprise talc, mica, silica, and the inorganic pigments such as titanium dioxide, iron oxide, ultramarine, zinc oxide and their equivalents. The fillers are present at 25-75% by weight and have at least 50% of the particles coated with lecithin to lower the surface energy of the fillers resulting in a smooth, ultra-fine emollient face powder. The lecithin coating on the nylon and fillers is typically 1-2% by weight but a range of 0.2 to 5% is permissable. The coating can be applied by any conventional technique. Lecithin-coated talc at a level of 2-50% by weight and lecithin coated mica at 5-20% by weight are the preferred fillers. The inorganic pigments need not be lecithin coated.

The blend of silicone oils comprising both a low molecular weight fraction of dimethicone and a high molecular weight fraction of dimethicone is present at a level of 1-10% by weight with 5-8% being preferred. The ratio of low molecular weight fraction to high molecular weight fraction is about 6:1 but a range of between 4:1 and 8:1 is operable. The low molecular weight dimethicone further coats the lecithin-coated particles thereby lowering the surface tension of these particles to give a very smooth feel to the touch. The high molecular weight dimethicone ensures that all dry fillers (without lecithin coating) are fully coated to produce maximum emolliency.

Another silicone oil (CFTA name dimethicone polyol) which has polyoxyethylene and polypropylene side chains may be used to solubilize fragrances or perfumes added to the face powder. In the case of a blush or eyeshadow addition of fragrances is not necessary.

DESCRIPTION OF THE PREFERRED EMBODIMENTS

The generic cosmetic pressed powder of this invention comprises the following parts by weight:

| | |
|---|---|
| Polyethylene | 1-6% |
| Polymethyl methacrylate | 1-10% |
| Lecithin-coated nylon | 15-25% |
| Lecithin-coated fillers | 25-75% |
| Dimethicone (1-500 cps) | 1-10% |
| Preservatives | 0.1-1% |

The powder component contains polyethylene, polymethyl methacrylate, and nylon as essential ingredients, and the nylon is preferably lecithin-coated. The lecithin-coated fillers generally comprise 20-50% talc and 5-20% mica. The inorganic pigments (included in the term "filler") need not be lecithin-coated. These pigments include iron oxide, titanium dioxide, ultramarine and other conventional pigments. Polyethylene, a low surface energy filler serves as a binder, but other conventional fillers, such as zinc stearate, may be added at the 1-4% level. The preservatives are conventional preservatives such as methyl paraben, propyl paraben, and ethyl paraben.

The above base and cosmetic prepared therefrom can be prepared by any of the art recognized techniques which give a uniform dispersion, such as high speed mill. To make the cosmetic compositions, all dry ingredients, except for the lecithin-coated powders are dry blended and pulverized to below 30 microns. The lecithin-treated powders are then added and mixed uniformly by a high speed mixer. Finally, all components of the oil phase are stirred together, added to the mix and dispersed to achieve a homogenous product. Any standard high speed stirring or homogenizing apparatus can be used to carry out the mixing operation.

The following examples are illustrative. In all of the examples, the above method of preparation was followed and the parts are parts by weight.

EXAMPLE 1

| COSMETIC PRESSED POWDER | |
|---|---|
| Polymethyl methacrylate | 8.00 |
| Lecithin/Nylon | 15.00 |
| Lecithin/Talc | QS |
| Lecithin/Mica | 15.00 |
| Polyethylene | 4.00 |
| Zinc stearate | 1.00 |
| Iron oxide black/bismuth oxychloride | 0.07 |
| Iron oxide yellow/talc | 0.64 |
| Iron oxide red/bismuth oxychloride | 0.35 |
| Bismuth oxychloride | 4.74 |
| Titanium dioxide/bismuth oxychloride | 2.30 |
| Ultramarine blue | 0.01 |
| Preservatives | 0.60 |
| Dimethicone (10 cps) | 3.10 |
| Dimethicone (9000 cps) | .50 |
| Perfume oil | 0.15 |
| Dimethicone copolyol | 0.04 |
| | 100.00% |

EXAMPLE 2

| COSMETIC LOOSE POWDER | |
|---|---|
| Polymethyl methacrylate | 8.00 |
| Lecithin/Nylon | 15.00 |
| Lecithin/Talc | QS |
| Lecithin/Mica | 15.00 |
| Polyethylene | 3.00 |
| Zinc stearate | 2.00 |
| Iron oxide black/bismuth oxychloride | 0.07 |
| Iron oxide yellow/talc | 0.64 |
| Iron oxide red/bismuth oxychloride | 0.35 |
| Bismuth oxychloride | 4.74 |
| Titanium dioxidide/bismuth oxychloride | 2.30 |
| Ultramarine blue/bismuth oxychloride | 0.01 |
| Preservatives | 0.60 |
| Dimethicone (10 cps) | 3.50 |
| Dimethicone (9000 cps) | 0.60 |
| Perfume oil | 0.15 |
| Dimethicone copolyol | 0.04 |
| | 100.00% |

EXAMPLE 3

| EYE SHADOW | |
|---|---|
| Polymethyl methacrylate | 8.00 |
| Lecithin/nylon | 15.00 |
| Lecithin/talc | QS |
| Lecithin/mica | 15.00 |
| Polyethylene | 5.00 |
| Zinc stearate | 1.00 |
| Iron oxide black/bismuth | 1.00 |
| Iron oxide yellow/talc | 2.00 |
| Iron oxide red/bismuth oxychloride | 0.50 |
| Bismuth oxychloride | 4.15 |
| Titanium dioxide/bismuth oxychloride | 2.00 |
| Ultramarine blue/bismuth oxychloride | 5.00 |
| Preservatives | 0.60 |
| Dimethicone (10 cps) | 3.50 |
| Dimethicone (9000 cps) | .50 |
| | 100.00% |

EXAMPLE 4

| COSMETIC CONCEALER | |
|---|---|
| Polymethyl methacrylate | 8.00 |
| Lecithin/nylon | 15.00 |
| Lecithin/talc | QS |

-continued
COSMETIC CONCEALER

| | |
|---|---|
| Lecithin/mica | 15.00 |
| Polyethylene | 4.00 |
| Zinc stearate | 1.00 |
| Iron oxide black/bismuth oxychloride | 0.30 |
| Iron oxide yellow/talc | 2.00 |
| Iron oxide red/bismuth oxychloride | 1.00 |
| Bismuth oxychloride | 2.86 |
| Titanium dioxide/bismuth oxychloride | 20.00 |
| Ultramarine blue/bismuth oxychloride | 0.10 |
| Preservatives | 0.60 |
| Dimethicone (10 cps) | 6.00 |
| Dimethicone (9000 cps) | 1.00 |
| Perfume oil | 0.10 |
| Dimethicone copolyol | 0.02 |
| | 100.00% |

While this invention has been described by specific examples, various changes and modifications may be made without departing from the spirit and scope thereof. The invention, therefore, is not to be limited except as defined in the following claims.

What is claimed is:

1. A cosmetic comprising 10-90% by weight of a powder component and 1-10% by weight of a silicone oil component wherein the powder component has a particle size less than 30 microns, at least 50% of said particles having, an average particle size of 10 microns, and at least 70% of said particles being coated with lecithin, the lecithin coating on any nylon or filler comprising 0.2-5%, said powder component comprising 1-10% by weight methylmethacrylate polymer having a particle size of below 10 microns, 5-25% by weight nylon polymer, 1-6% by weight polyethylene and 25-75% by weight fillers, said nylon and fillers having a particle size below 20 microns; at least 50% of the filler being coated with lecithin; and wherein the silicone oil component is a blend of low and high molecular weight dimethyl polysiloxane polymers at a ratio of 4:1 to 8:1, the blend having a viscosity of 10-500 centipoises.

2. The cosmetic of claim 1 wherein all the particles of the powder component are less than 20 microns.

3. The cosmetic of claim 2 wherein the nylon particles are spherical in shape, have an average particle size of 10 microns and are coated with lecithin.

4. The cosmetic of claim 3 wherein the filler comprises 20-50% by weight lecithin-coated talc.

5. The cosmetic of claim 4 wherein the filler comprises 5-15% by weight lecithin-coated mica.

6. The cosmetic of claim 5 wherein the blend of dimethicone oils in the oil component comprises an oil having a viscosity of 4000-11000 centipoise and an oil having a viscosity of 1-10 centipoises.

7. The cosmetic of claim 6 wherein 1-4% by weight zinc stearate is present as a binding agent.

8. The cosmetic of claim 6 wherein the oil component contains a fragrance oil solubilized in dimethicone copolyol.

9. The cosmetic of claim 7 comprising an eye shadow.

10. The cosmetic of claim 8 wherein the powder is a face powder.

11. The cosmetic of claim 10 wherein the face powder is loose powder.

12. The cosmetic of claim 10 wherein the face powder is pressed powder.

13. The cosmetic of claim 10 wherein the face powder is a concealer.

* * * * *